United States Patent [19]

Kopala et al.

[11] Patent Number: 4,919,128
[45] Date of Patent: Apr. 24, 1990

[54] NASAL ADAPTOR DEVICE AND SEAL

[75] Inventors: John A. Kopala; John E. Remmers, both of Calgary, Canada

[73] Assignee: University Technologies International Inc., Alberta, Canada

[21] Appl. No.: 236,941

[22] Filed: Aug. 26, 1988

[51] Int. Cl.⁵ .................... A61M 15/00; A61M 16/06
[52] U.S. Cl. ......................... 128/207.18; 128/205.25
[58] Field of Search ................ 128/203.22, 204.11, 128/204.18, 204.12, 205.25, 206.21, 206.27, 207.13, 207.18, 207.17, DIG. 26

[56] References Cited

U.S. PATENT DOCUMENTS

| 844,097 | 2/1907 | Caldwell | 128/203.22 |
| 2,185,997 | 1/1940 | Heidbrink | 128/207.18 |
| 2,292,568 | 8/1943 | Kanter et al. | 128/203.28 |
| 2,383,649 | 8/1945 | Heidbrink | 128/206.27 |
| 2,664,084 | 12/1953 | Hammermann | 128/204.11 |
| 2,831,487 | 4/1958 | Fafilaw | 128/DIG. 26 |
| 4,151,843 | 5/1979 | Brekke et al. | 128/205.25 |
| 4,782,832 | 11/1988 | Trimble et al. | 128/207.18 |

FOREIGN PATENT DOCUMENTS 608528  7/1926  France ............... 128/204.11

Primary Examiner—Edgar S. Burr
Assistant Examiner—Kimberly L. Asher
Attorney, Agent, or Firm—Burns, Doane, Swecker & Mathis

[57] ABSTRACT

A nasal adaptor device and seal for delivering gases under pressure to the nasal airway of an individual including an aerodynamically contoured manifold to receive gases from an inlet and to divide the gases for flow to a pair of flange members, preferaly having a non-spherical curved "egg-shaped" surface, which members are, complementary to the nares of an individual without cannulating the nares to provide a seal to withstand positive pressure of gases to be distributed to the nasal airways. The devices and nares seals of this invention are especially useful in treatment of obstructive sleep apnea and in ventilation of individuals for whom positive pressure ventilation is indicated.

20 Claims, 2 Drawing Sheets

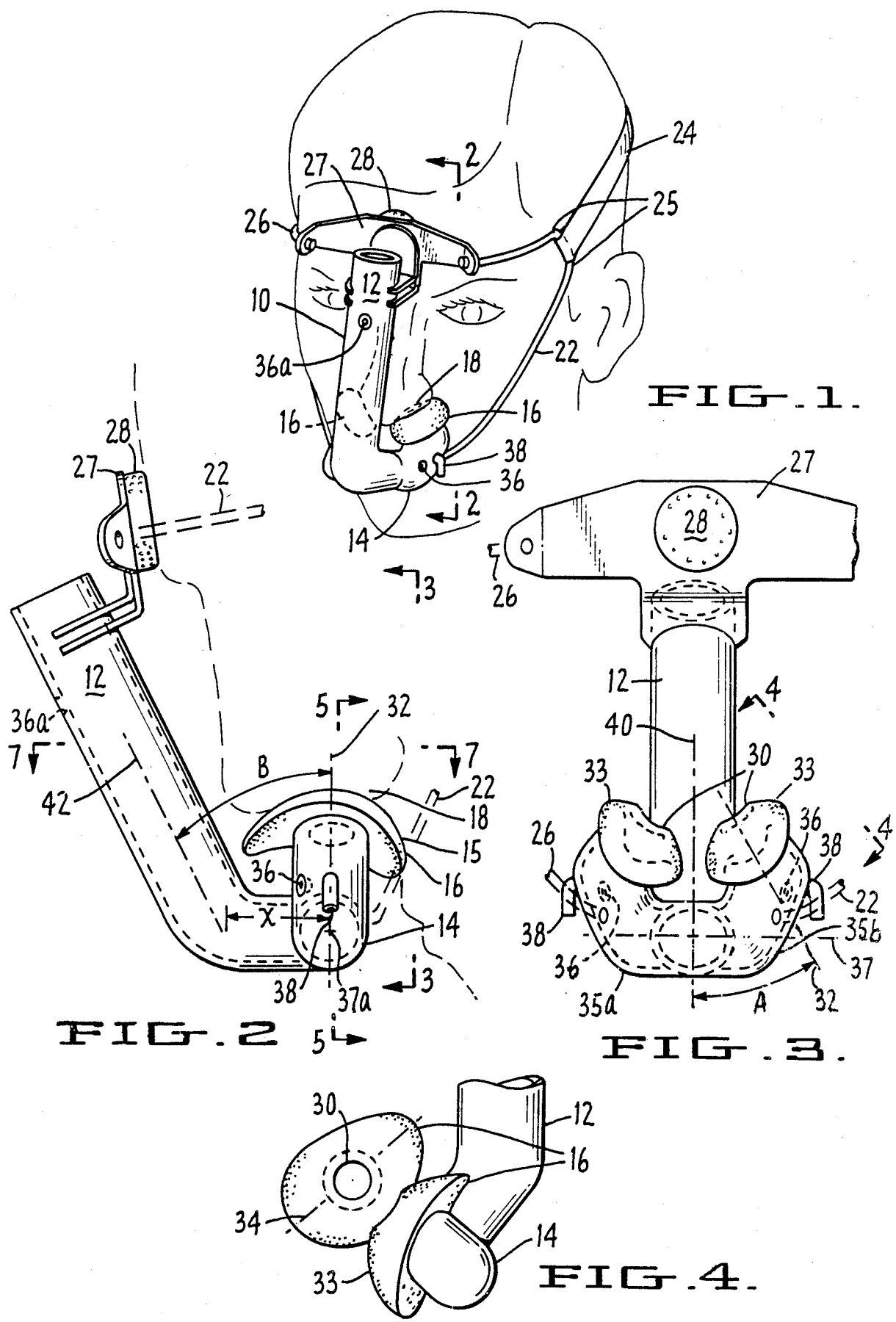

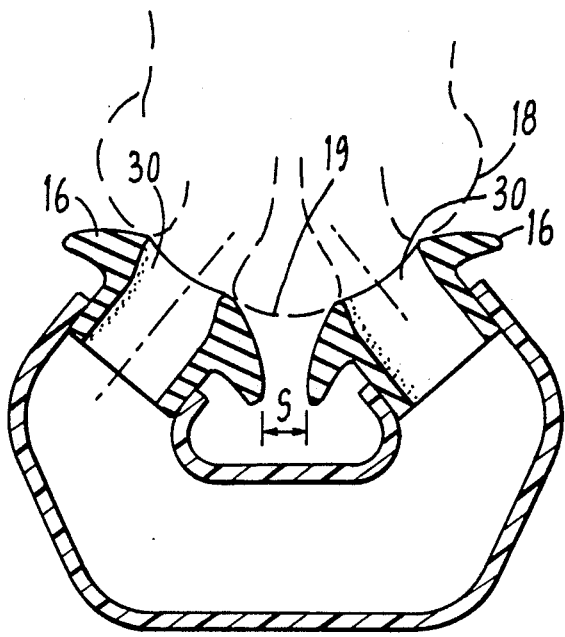
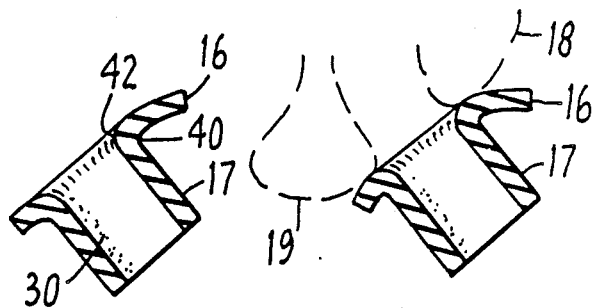
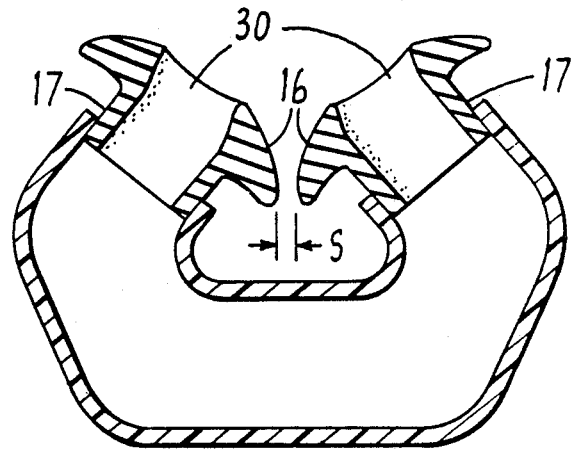
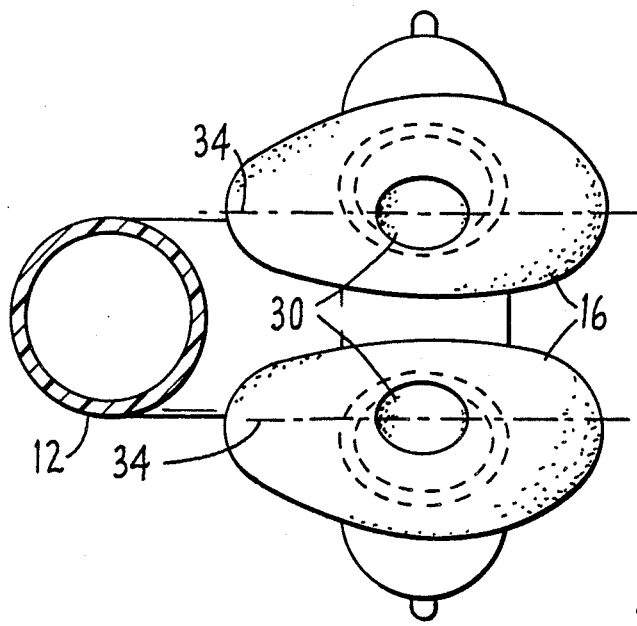
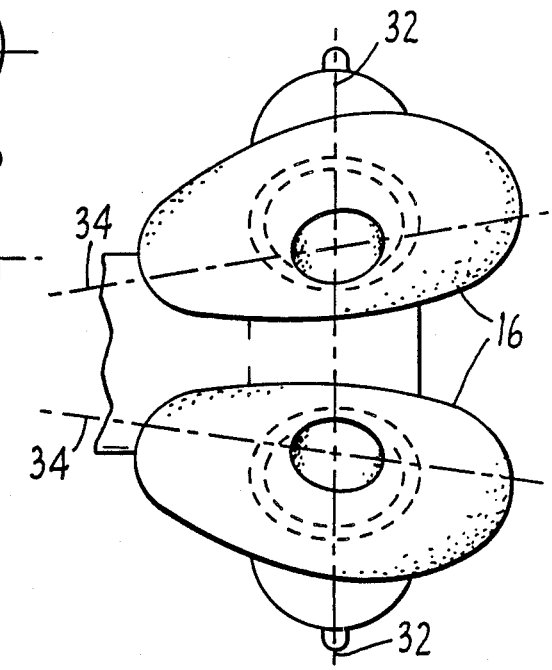

NASAL ADAPTOR DEVICE AND SEAL

FIELD OF THE INVENTION

The invention relates to devices for delivering gases to the nasal airway at pressures at or above ambient pressure.

BACKGROUND OF THE INVENTION

In the past, various devices have been developed to transmit gaseous or liquid media at atmospheric pressure from a tube to the internal nasal passages. Such devices generally consist of masks which clamp over the external nasal area or tubes which cannulate the nasal airway. Today, it is highly desirable to transmit air to the nasal passages under pressures greater than atmospheric pressure with a device that is comfortable to wear and which provides a leak-free seal between the device and the nostrils. For certain disorders, such as obstructive sleep apnea, it is important to have a device to deliver air in a free-flowing manner under positive pressure to the nasal air passage of a sleeping individual, and in order to do so, the device must be both comfortable and maintain a seal despite a variety of movements of the head, when the individual is exerting no action to retain the device in position. It is therefore desirable to have a device that is self-retaining and can be tolerated for prolonged periods while providing an adequate seal with the nostrils of an individual.

Many of the prior art devices establish a seal with the nasal airway by insertion of a tube or the bulbous portion of a tube into the nasal air passage. This cannulation of the nasal airway is unacceptable for long-term use, particularly during sleep, inasmuch as any contact of a foreign substance with the internal surface of the nose causes discomfort and nasal and lachrymal secretions.

It would therefore be desirable to have a device that would contact the nostrils, also used interchangeably hereinafter with "nares", and seal to withstand positive pressure, the device being selfretained and presenting aerodynamically contoured, low-resistance pathway for transmission of gases, thereby minimizing the fluctuations of pressure at the nares.

SUMMARY OF THE INVENTION

The purpose of the instant invention is to provide a nasal adaptor device and seal for delivering gases under pressure to the nasal airway. To accomplish this purpose, there is provided a device and seal as a part thereof having flange members to contact the nares of an individual to receive gases, the seal having a non-spherical surface which because of its surface configuration and port is complementary to the external nares of the individual and establishes a seal with no discomfort.

In one aspect of the invention there is provided a nasal adaptor device for delivering gases under pressures to the nasal airway comprising:

an inlet means to receive gases to be delivered;

manifold means connected to said inlet means to divide the flow of gases that may flow through said inlet means into said manifold means, said manifold means being aerodynamically contoured to provide a low-resistance pathway to direct and guide gases to be distributed;

seal means connected to said manifold means, said seal means contacting the nares of an individual to receive gases and being complementary to the nares of an individual without cannulating such nares to provide a seal to such nares to withstand positive pressure of gases to be distributed; and retaining means operatively connected to said seal means to maintain contact between said seal means and the nares of an individual without undue discomfort to the individual.

Another aspect of the invention is a nasal adaptor seal comprising a pair of flange members, each having a convex surface, each having a portal therethrough for supplying air to the nasal airways, the portals being positioned to correspond to the nasal openings; the axis of each portal being positioned in effective alignment with the aerodynamic air flow into and out of the nasal airways, said convex surfaces being complementary to the nares of an individual without cannulating such nares, the perimeter of said surfaces generally corresponding to a projection of the external meatus of the nares of an individual.

Another aspect of the invention is a nasal adaptor seal comprising a pair of flexible flange members, each having a deformable surface, each having conduit means on the opposite side from said surface adapted for attachment to a gas manifold means, each having a portal therethrough for supplying air to the nasal airways, said flange member having a perimeter generally corresponding to a projection of the external meatus of the nares of an individual, said surface of said flange member being conformable upon contact with the nares of an individual whereby said surface is deformed into a convex shape complementary to the nares of an individual without cannulating such nares and being so conformable by application of such flange member against such nares with a force which does not cause undue discomfort to the individual. Preferably the conduit means between each flange and the gas manifold is flexible, thereby assisting in the flanges being positioned on and aligned with the nares.

In another aspect this invention provides a breathing device in combination with retaining means for holding the device in place on the face of an individual and adapted to fit around the head of the individual wherein the retaining means comprises a pair of flexible members, one end of each attached to a lower portion of the breathing device and the other end of each attached to an upper portion of the breathing device, the central portion each adapted to extend laterally from the breathing device, a third flexible member movably attached at one end to the central portion of the first flexible member and movably attached at the other end to the second flexible member and adapted for being placed around the back of the head of the individual, whereby the movable attachments allow adjustment of the position of the third member along the central portion of each of the first and second flexible members to thereby provide means for adjustment of the respective retaining forces on the upper portion and lower portion of the breathing device against the face of the individual.

DESCRIPTION OF THE DRAWING

FIG. 1 is a perspective view of the nasal adaptor device secured to the head of an individual.

FIG. 2 is a side view taken along line 2—2 in FIG. 1.

FIG. 3 is a back view of the invention taken along line 3—3 in FIG. 2.

FIG. 4 is a partial perspective view illustrating details of the seal of the nasal adapter device taken along line 4—4 in FIG. 3.

FIG. 5 is a cross-sectional view taken along section line 5—5 in FIG. 2, illustrating contact of the flange members of the seal of the instant invention in contact with the nasal passages of an individual, shown in phantom.

FIG. 6 is a cross-sectional view similar to FIG. 5 illustrating the telescoping capability of the flange members.

FIG. 7 is a partial perspective and cross-sectional view taken along line 7—7 in FIG. 2.

FIG. 8 is a view similar to FIG. 7 illustrating the rotatability of the flange members.

FIG. 9A is a cross-sectional view of an illustration of an embodiment of a flexible flange member.

FIG. 9B is a cross-sectional view similar to FIG. 9A positioned in contact with the nasal passage (shown in phantom) of an individual.

DESCRIPTION OF PREFERRED EMBODIMENT

The instant invention provides a device which can be used to supply room air or oxygen-enriched air to the external opening of the nasal airway under a constant pressure which exceeds that acting upon the surface of the body. This produces a pressure within the upper airway that is greater than ambient pressure acting upon the external surface of the neck and thereby distending or opening the pharyngeal airway. By this action, the positive pressure delivered to the nasal airway by the device can be used to open the pharyngeal airway of individuals with obstructive sleep apnea while they sleep. This approach is considered to be the best available treatment of this disorder. Because of the seal provided at the nares, the device also can be used to deliver cyclicly varied pressure to assist the breathing of patients with impaired capacity for ventilation.

The device of the instant invention provides a unique structure suitable for easy and quick fitting to an individual and capable of supplying positive pressure air, oxygen or a mixture thereof to the nasal airway of the individual without discomfort to the individual. This structure comprises (a) seal means for complementarily contacting with and sealing to the nares of an individual without cannulating such nares, (b) manifold means for connecting the seal means to an inlet means, (c) inlet means adapted for supplying gases to the manifold means and for positioning above, substantially centered on and approximately parallel to the nose of the individual, (d) support means connected to the upper portion of the inlet means and adapted to rest on the forehead of the individual, and (e) retaining means for retaining the device in position on the individual. The device of this invention having the above structure, as illustrated by the embodiments discussed herein, has a number of unexpected advantages over prior art devices. The individual wearing this device does not have claustrophobic feelings, as are felt when wearing masks and other devices. The individual's vision is not impaired because the inlet means is positioned parallel to and centered on, but not touching, the bridge of the nose. Thus, the inlet means is between the line of vision of the individual's eyes and does not block the vision of either eye. This position of the inlet means also allows the individual to wear eyeglasses, which may be essential for reading or watching television. The feelings of comfort and freedom afforded by the device of this invention are in part due to the fact that the device contacts the face of the individual only at the nose and the forehead, plus the retaining means. In contrast, masks and other prior art devices cover a significant portion of an individual's face. Since the device of this invention does not involve substantial facial contact or coverage, it is effective on individuals with beards and mustaches, which frequently interfere with effective use of masks and prior art devices. Moreover, the device of this invention eliminates much of the irritation suffered by individuals with skin conditions which masks tend to create or aggravate.

The device of this invention includes a seal means which seals to the external part of the nares without cannulating the nostril. This feature provides comfort for the individual because the seal means contacts only the tougher exterior skin of the nose at the meatus and not the sensitive internal mucous membranes of the nose. Thus, this device provides an effective positive pressure seal and provides improved comfort for the individual. The improved comfort is due to the fact that only a small area of skin is contacted by this device and because the nasal passages are not cannulated, compared, respectively, to the large areas of skin covered by masks and the prior art cannula devices.

The instant invention creates a seal with the human nasal airway by applying a curved sealing flange member onto the external meatus of each nostril. The flange member which is complementary to the nares of the individual comprises a pair of flange members perforated by a circular port. Such complementary flange member includes flange members which are conformable to be complementary to the nares. The particularly unique flange member provided by this invention is characterized by the port opening being positioned inside the perimeter of a compound ellipsoid, the perimeter being inscribed by the projection of each external nasal meatus onto a non-spherical, egg-shaped type surface. When these unique flanges are pulled cranially and dorsally, their surfaces seat in complementary fashion onto the external meatus of the nares without cannulating the nares, thereby forming a seal capable of withstanding 30 to 40 cms of water nasal positive pressure without a leak. The device and seal (flange) of the instant invention takes advantage of the elastic properties of the nostrils distal to the nasal bones and of the relative constancy of size of the nasal septum and the shape of the external meatus to achieve a competent seal in a wide variety of individuals. As the flange members are pulled upward and backward, the orifice of each nostril is stretched, and forces are distributed evenly over the perimeter causing the nostril to expand and conform to the curved surface. The upward, medial and backward forces exerted on the surface of a flange member are countered by oppositely directed forces developed in the walls of the nostril causing the external orifice of the nares to be tightly applied to the surface of the flange member. The device also takes advantage of the relatively thin wall of each nasal airway. This thin wall means that a relatively small force in the wall of the nasal airway is transformed into a relatively large surface pressure where the external meatus is applied to the surface of the sealing flange. This relatively large pressure means that substantial intra-nasal pressures can be developed before the seal becomes incompetent. For a leak to occur, cavitation must occur between the nostril's surface and the surface of the flange member.

A key feature of the device is that a seal is formed by contact of the surface of the flange member with the skin of the nostril. That is, the device does not touch the internal mucous membranes of the nose. This restricted contact is essential for at least two reasons: first, stimulation of pressure and touch receptors of the external skin is well tolerated, whereas pressure of an external object on the internal mucous membranes of the nose is noxious, painful and unpleasant, often eliciting secondary reflexes, e.g., tearing and nasal hypersecretion; and second, the skin of the external nostril is highly durable, so that prolonged contact with a foreign substance under modest pressures causes no deterioration in the surface, whereas the mucous membrane breaks down and erodes under conditions of prolonged contact with foreign objects. Thus, the curved sealing flange of the instant invention can be used comfortably and repeatedly for long periods. By contrast, a device which forms a seal between an external tube and the nasal airway by contacting the mucous membrane of the under-surface of the internal nasal air passage causes pain and degrades the surface of the air passage when used repeatedly or for prolonged periods. Such mucous membrane contact also allows increased risk of infection.

In the description of the present invention above and in the following particular embodiments, it will be recognized that various configurations and embodiments can be constructed incorporating the nasal adaptor seals and the nasal adaptor devices of the present invention. In addition, it will be recognized that the seals and devices of this invention can be sized for adult, juvenile or infant use.

With reference to the drawings, FIG. 1 illustrates the nasal adaptor device shown generally at 10 secured to the head of an individual. Device 10 includes an inlet means 12 to receive gases to be delivered, manifold means 14 connected to the inlet means 12 to divide the flow of gases that may flow through the inlet means, and seal means in the form of flange members 16. As will be later appreciated, the manifold means 14 is aerodynamically contoured to provide a low-resistance pathway for gases to be distributed.

Flange members 16 are preferably movably connected to the manifold means 14. As can be seen in FIGS. 1 and 2, the flange members 16 contact the nares 18 of the individual and are complementary to the nares of the individual without cannulating the nares to provide a seal that will withstand substantial positive pressure of gases to be distributed.

The device of this invention can be used with conventional means for retaining it in proper position on the individual. However, FIG. 1 illustrates a preferred retaining means which comprises a pair of straps 22 and 26 operatively connected to the flange members 16 via the manifold means 14 and inlet means 12 via the forehead support strut 27 to maintain contact between the flange members and the individual without undue discomfort to the individual. The retaining means further comprises a strap 24 that can be placed around the back of the head of the individual, usually above the ears of the individual, and is connected to said first strap 22 and the second strap 26 which are connected to manifold means 14 and the upper portion of the inlet means 12, such as by support means 27. In this configuration, strap 24 can be adjusted up or down at attachment area 25 on straps 22 and 26 in order to adjust the distribution of the retention force on the forehead versus the nose of the individual. A preferred embodiment of this retaining means comprises straps 22 and 26 having a small cross section which cover less surface area of the facial area and a wider strap 24 for the comfort on the back of the individual's head.

Inlet means 12 preferably comprises an air supply tube which is connected to the manifold means 14 at one end of the air supply tube and support strut 27 near the other end, which support strut has pad 28 adapted to contact the forehead of an individual. Support strut 27 can preferably be adjustable in position along the upper length of inlet tube 12 to provide additional adjustment to fit the particular size and shape of the individual's head. It can be seen in FIG. 2 that the air supply tube is spaced from the bridge of the nose of an individual so as not to unduly impair vision of the individual and to allow eyeglasses to be worn when the device is in proper position on the individual's head.

For the typical adult application, the inlet tube of the inlet means 12 has a preferred internal diameter of 16 mm and connects to manifold means 14 having an internal diameter of 13 mm. Manifold means 14 terminates in the seal means. The seal means comprises a pair of flange members 16, each flange member 16 having a surface 33 which can be a spherical type surface, but preferably comprise the above described unique non-spherical "egg-shaped" type of surface. The curved surface of each flange member 16 has a portal through the curved surface, the portal having an axis 32, as can be seen in FIG. 3, corresponding generally to the axis of gas that may flow through the portal 30. The portals 30 are preferably from about 10 mm to about 12 mm in diameter and are usually centered in the curved surface. The perimeter of curved surface 33 of the flange members 16 generally corresponds to a projection of the external meatus of the nares of an individual. The "egg-shaped" flange member has a longitudinal axis 34 taken along the long dimension of the egg shape. As seen in FIG. 4, each portal 30 is preferably centered on axis 34. It should be noted that portal 30 may be centered in surface 33, but in some embodiments it is preferable that surface 33 extend further toward the center of the device, i.e., more surface area toward the septum or the upper lip of the individual, with less surface area toward the outside or front of the device. While the centered configuration is generally acceptable, the asymmetrical configuration can provide for some individuals improved comfort and stability, can provide reduced mass or bulk, and provide preferred esthetics at the side areas of the nose. Additional surface at the rear portions of the flanges can provide particular comfort and/or stability of the device on an individual because the rear portion of flange 16 rests on the upper lip of the individual as shown at region 15 in FIG. 2.

The flanges useful in this device may be a rigid, inflexible material, and can be spherical in shape to provide the desired seal which is complementary to the nares without cannulating the nares. In this case, the positive pressure seal is provided by the pliability of the nares themselves. However, in preferred embodiments, the flanges are made of a flexible material, such as a silicone rubber. The flanges should be sufficiently pliant to easily conform to the nares, but not so soft that the flange can collapse or cannulate the nose. In a preferred form, the flange materials provide some flexibility, but is firm enough to cause some conforming of the nares to the flange to provide the optimum and most comfortable seal by the flange being complementary to the nares. In preferred embodiments the flange will also have the unique "egg-shaped" surface provided by the flanges of this invention.

FIG. 3 illustrates exhaust outlet means in the form of outlets 36 which are appropriately sized, e.g., 2.75 mm in diameter, and are positioned in each arm of the manifold means 14. The outlet means 36 can be positioned between the flange members 16 and inlet means 12 to minimize the distance between the exhaust outlet means 36 and the flange members 16 to minimize the rebreathing of expired air. Outlets 36 are preferably directed away from patient's face and body and may be positioned close to the flange members 16 for aerodynamic efficiency. Conventional sizing and positioning of the exhaust ports, such as used in masks for similar applications, can be used in the present invention. It has been found, however, that a conically tapered (exterior countersunk) exhaust port, as shown at 36 in FIG. 2, provides reduced noise and increased aerodynamic efficiency (lower resistance) and is preferred by some individuals. Optionally, a single exhaust port, appropriately sized (e.g., 4 mm), can be located in inlet tube 12, as shown at 36a in FIG. 2, instead of the two ports 36 as shown. A single exhaust port on inlet means 12 can have the advantage of having the exhaust flow more remote from the individual's face.

A key aspect of an individual's acceptance of nasal airway positive pressure is the absence of any sensation of an impediment to breathing caused by pressure fluctuations in the nose during breathing. The device of the instant invention is aerodynamically designed, i.e., the manifold means is designed to minimize fluctuations in the nares' pressure during breathing. Three features of the device combine to keep these fluctuations less than 1 cm of water, about half that previously observed in nose masks used for the same medical purpose. These features are: (1) low resistance of the conducting tubing, the diameter of the manifold means being selected to produce the same resistance as the inlet tube; (2) the exhaust outlet means being relatively large, allowing a high flow during expiration with little increase in pressure; and (3) the bias flow is relatively large and is directed at the nostril's orifice so that the kinetic energy of the stream of gas contributes significantly to the pressure at the portal. This high flow system does not preclude the use of supplemental oxygen, when needed. In fact, this device provides increased efficiency of oxygen use, because the oxygen can be injected into the manifold means 14 close to the flange members where it is not diluted by the bias flow. The best aerodynamic flow will be achieved using gentle sweeping curves to direct the flow of gas to the nasal passage along the axis 32 of portal 30. For example, for optimum aerodynamic flow, the use of a Y junction at manifold 14 may be preferred over a T junction because of the decreased resistance. However, a T junction may be desired, where it provides sufficiently low resistance, because a T configuration also can provide convenient additional means of adjusting the device to fit various individuals. As shown in FIGS. 2 and 3, the individual left and right sides 35a and 35b of the manifold means 14 can be made rotatable about axis 37 in FIG. 3 and point 37a in FIG. 2 where axis 37 and projected axis 32 intersect, thereby providing additional adaptability for fitting this device to various individuals.

In FIG. 2 optional oxygen inlet means 38 are provided so that an oxygen supply can be connected to the manifold in order to inject oxygen into the manifold means 14 close to the flange members 16. The oxygen inlet means is a valve type means which opens only when an oxygen supply is connected thereto. This arrangement in the device of this invention provides a very efficient means for supplying oxygen to an individual.

As seen in FIG. 3, the nasal adaptor device 10 has a longitudinal or vertical plane 40 which bisects the device and corresponds to the vertical centerline of the device. It can be seen that axis 32 of each portal is positioned at an angle A, which is preferably 30°, to the vertical centerline plane 40 of the device to provide optimum fit for conforming contact of the flanges to the nares and to provide a low resistance pathway for gases to be distributed through manifold 14 and portals 30. This relationship may also be described by saying that the portal axes 32 are non-parallel and are inclined toward each other at an angle of A of approximately 40° relative to a common vertical plane 40 that would intersect each portal axis 32. Angle A may be varied by about ±10°, but normally if varied from 30° will preferably be more than 30°, such as about 35° or about 40°.

As seen in FIG. 2, there is also a relationship, angle B, between the portal axis 32 (projected to the side view plane) and the inlet tube longitudinal axis 42. This angle B will usually be between about 25° and about 30°, normally about 28°. This angle is somewhat adjustable depending upon the position of forehead support strut 27 and the thickness of forehead pad 28 arrangement, as well as the distance the air supply tube 12 is to be positioned above tip of the nose of the individual. Angle B can be adjusted to provide the desired position of inlet tube 12 above the nose of the individual while maintaining the desired position of portal axis 32 for smooth air flow into the nasal passages. As mentioned above, this adjustment can be by rotation about axis 37. This angle B can also be adjusted by changing the length X of the lower portion of inlet means 12, without changing the relationship of axis 32 of portal 30 to the nasal airway. Changes in length X of the lower portion of inlet means 12 can be made, e.g., by telescoping means, to adjust the distance between inlet means 12 and the tip of the nose. Adjustment by rotation about axis 37 is convenient and preferred, to the extent that axis 32 of each portal remains sufficiently aligned with the nasal airways to maintain the desired aerodynamic air flow.

It can be appreciated that in the present device the spacing of the inlet means 12 above the nose of the individual overcomes a number of disadvantages of prior art devices. With the present invention eyeglasses can be worn underneath the device because the inlet tube is positioned above the bridge of the nose and does not interfere with the wearing of eyeglasses. Likewise, inlet tube 12 is centered and positioned vertically above the bridge of the nose so that it does not unduly impair the vision of the individual. Consequently, the present invention essentially eliminates much of the feelings of claustrophobia associated with prior art mask-type devices and eliminates the discomforts associated with prior art cannula-type devices.

It will also be appreciated that the device of the present invention overcomes other disadvantages of prior art devices. For example, the present device provides an air-tight seal for positive pressure air flow on all individuals. The prior art mask-type devices do not provide a sufficient positive pressure seal on individuals with mustaches, beards or atypical facial features. The present device provides a good seal on those individuals as well, because of the direct seal of surface 33 of flange member 16 to the nares of the individual. Other advantages will be apparent to those skilled in the art.

FIGS. 5-8 illustrate the adjustability of the flange members 16. Since the 30° angle A of the portal axis 32 and the position of the flange surface are somewhat critical, the distance between the flanges 16 can be made adjustable by telescoping each individual flange member 16 with respect to manifold means 14. The flange members 16 telescope generally along portal axis 32 to adjust the distance S between the flanges 16, and, consequently, the distance between portals 30, in order to compensate for and accommodate the differences in shape and size of septum 19 in various individuals, and to accommodate individuals with a wide variety of nose configurations. In this way, the preferred 30° angle A shown in FIG. 3 is maintained while adjusting the distance between the two flange members 16. The telescoping of the flange members 16 can be seen by a comparison of FIGS. 5 and 6.

Another preferred aspect is illustrated in FIGS. 5 and 6 in that flange members 16 and the stems 17 of flange members 16 may be of flexible material, e.g., silicone rubber, to provide additional comfort and ease of fitting. In such an embodiment, flange 16 and stem 17 flex to conform to the nose of the individual. If preferred, the telescoping and flexible flange 16 and flexible stem 17 features may be combined for optimum fitting of individuals.

FIGS. 7 and 8 illustrate rotation of the flange members 16 to further accommodate the wide variety of nose configurations in individuals. Depending on the shape of the nares of an individual and shape of the nasal openings, it may be desirable to rotate flange members 16 about the portal axes 32 to better fit the individual comfortably. FIG. 8 shows flange members 16 rotated to bring the small ends of the flanges, which are near the tip of the nose of the individual, closer together and the ends of the flanges near the face further apart. If desired, flange members 16 can be rotated in opposite directions for better comfort and seal on some individuals.

FIGS. 9a and 9b illustrate in cross-section an alternative preferred embodiment of the flange member 16 of this invention. In this embodiment, the flange member is a thin-wall construction of flexible, resilient material and capable of deforming into the desired shape which is complementary to the nares of an individual. In this embodiment, the flange member can have an initial slightly convex shape as shown in FIG. 9a (or can be flat or even concave), but is deformed upon contact with nares 18 to the more convex shape surface as shown in FIG. 9b. The perimeter of the flange can be circular, elliptical or egg-shaped; thus the flange member, when deformed to the convex shape in use, will be spherical or egg-shaped, respectively. The elastic material for the flange member in this embodiment should be soft enough and sufficiently flexible to easily conform to the nares of an individual with low enough force so that the pressure of the flange against the nares is comfortable for the individual. But, the material should not be so soft that the outer periphery of the flange is not capable of holding the desired positive pressure seal with the nares and should not be so soft to allow the flange to collapse to the point where it might tend to cannulate the nose. A preferred perimeter shape of the flange is egg-shaped so that when it is in its deformed in-use shape, it will assume a shape wherein the surface is at least in part shaped similarly to surface 33 in FIGS. 3 and 4. Other preferred features shown in FIG. 9A are the fillet 40 at the inside corner between stem 17 and flange 16, and the radius 42 on the shoulder at the end of portal 30. These features aid in the comfort and ease of the fit on the individual. In particular, the radiused shoulder 42, which gives the inside of the portal a trumpet type shape at the end, not only provides added fitting comfort for many individuals but also provides a more comfortable air flow pattern between the portal and the nasal airway. This is believed to to be due to a reduction in velocity of the air as it leaves the portal, which reduces any tendency of the air to dry out the interior nasal airway. The outside or maximum diameter of the trumpet shape at the end of portal 30 should not exceed the size of the nasal airway opening at the nares. As shown in FIGS. 9a and 9b the portion of flange 19 under the septum can be shorter than on the opposite side of portal 30. In a preferred embodiment, the portions of flanges 16 under the septum are shaped and positioned so that they do not pinch the septum between them, but rather push directly against the exterior surface of the septum and conform in shape to be complementary to the septum surfaces as well as the remainder of the nares. Also, in a preferred embodiment the portion of flanges 16 under the septum area can be sized and positioned such that they touch or very nearly touch. This configuration helps assure that the septum is not pinched between flanges 16 and that flanges 16 contact the surface area of the septum in a manner comfortable for the individual, especially for long wearing times. It should be noted also that these features can be further combined with previously mentioned features, particularly the flexible stem 17, to further enhance the comfort and ease of fit for each individual while providing the effective positive pressure seal which this invention uniquely furnishes in an efficient manner. The curvature of the surface 33 of a flexible flange 16 will be formed by and determined by the shape of the individual's meatus at the nares.

Although the present invention has been described with particular reference to a preferred embodiment, such disclosure should not be interpreted as limiting. Other alternatives and modifications will no doubt become apparent to those skilled in the art after having read the preceding disclosure.

What is claimed is:

1. A nasal adaptor device for delivering gases under pressures to the nasal airway comprising:
   an inlet means to receive gases to be delivered;
   manifold means connected to said inlet means to divide the flow of gases that may flow through said inlet means said manifold means being aerodynamically contoured to provide a low-resistance pathway to direct and guide gases to be distributed;
   seal means connected to said manifold means, said seal means contacting and being deformed by the nares of an individual to receive gases and being complementary and conformal to the nares of an individual without cannulating such nares to provide a seal to such nares to withstand positive pressure of gases to be distributed, said seal means comprising a pair of flexible flange members, each flange member having a curved surface which is generally "egg-shaped" presenting an area supported by the exterior surface of the nares of an individual including the septum without pinching the septum, each of said flange members having a portal through said curved surface for supplying air to the nasal airways, each portal being positioned to correspond to one of the nasal openings, the axis of each portal being positioned in effective alignment with the aerodynamic air flow into and out of the nasal airways; and retaining means operatively connected to said seal means to maintain contact between said seal means and the nares of an individual without undue discomfort to the individual.

2. A device as in claim 1 wherein the perimeter of the curved surface of a flange member generally corresponds to a projection of the external meatus of the nares of an individual.

3. A device as in claim 2 wherein the said portal axis of each portal being positioned at an angle between about 20° and about 40° from a vertical plane which bisects the device between the left half and the right half.

4. A device as in claim 3 wherein the angle between the longitudinal axis of said inlet means and said portal axis being positioned between about 25° and about 30°.

5. A device as in claim 2 wherein said flange members are rotatable generally about said respective portal axes and said flange members being adapted to telescope along said portal axes to adjust said flanges to accommodate a variety of nose configurations of various individuals.

6. A device as in claim 2 comprising exhaust outlet means in said manifold means positioned between said flange members and said inlet means to minimize the distance between said exhaust outlet means and the inlet means of gases to be delivered.

7. A device as in claim 2 comprising exhaust port means in the inlet means.

8. A device as in claim 2 further including oxygen inlet means in said manifold means.

9. A device as in claim 2 wherein the angle between the longitudinal axis of said inlet means and said portal axis being positioned between about 25° and about 30°.

10. A device as in claim 9 wherein said inlet means is connected at one end to said manifold means and has a pad near the other end of said inlet means, said pad adapted to contact the forehead of an individual, said inlet means being centrally positioned and spaced from the bridge of the nose and the tip of the nose of an individual, said inlet means thus positioned and spaced so as not to unduly impair the vision of an individual and to allow eyeglasses to be worn by the individual.

11. A device as in claim 10 wherein said retaining means includes a first strap that can be placed around the back of the head of an individual above the ears of such an individual and connected to a pair of straps each connected to said manifold means and to said pad adapted to contact the forehead of the individual.

12. A nasal adaptor seal comprising a pair of flexible flange members, each having a curved surface and each having a portal therethrough for supplying air to the nasal airways, the portals being positioned to correspond to the nasal openings, the axis of each portal being positioned to substantially align with the aerodynamic air flow into and out of the nasal airways, said curved surfaces being complementary and conformed to the nares of an individual upon contacting the nares of an individual under sufficient force to form a seal between the flange members and the nares and without cannulating such nares, the perimeter of said surfaces generally corresponding to a projection of the external meatus of the nares of an individual.

13. A seal as in claim 12 wherein each surface is convex and the portal axes are positioned at an angle of between about 20° and about 40° to a common vertical plane bisecting the distance between the flange members.

14. A seal as in claim 13 wherein flange members are each adapted to telescope generally along each portal axis to move said flange members and the portals therein toward and away from each other.

15. A seal as in claim 14 wherein said flange members are adapted to rotate generally about each portal axis.

16. A seal as in claim 12 wherein each said curved surface is "egg-shaped" having a longitudinal axis taken along the long axis of said egg shape, said portal of each said flange member being eccentrically positioned with respect to said longitudinal axis of the curved surface.

17. A seal as in claim 13 wherein each said curved surface is "egg-shaped" having a longitudinal axis taken along the long axis of said egg shape, said portal of each said flange member being eccentrically positioned with respect to said longitudinal axis of the curved surface.

18. A seal as in claim 17 wherein said flange members each telescope generally along each portal axis to move said flange members toward and away from each other.

19. A seal as in claim 18 wherein said flange members rotate generally about each portal axis.

20. A nasal adaptor seal comprising a pair of flexible flange members, each having a portal therethrough, each being sufficiently elastic and flexible to be capable of forming curved surfaces, the curvature of each of said surface caused by contact with the nares of an individual under sufficient force to form a seal between the flange members and said nares said curved surfaces being complementary to the nares of an individual without cannulating such nares, the perimeter of said surfaces generally corresponding to a projection of the external meatus of the nares of an individual, each curved surface being generally "egg-shaped" presenting an area supported against the exterior surface of the nares of an individual including the septum without pinching the septum.

* * * * *